US011781181B2

(12) United States Patent
Nagai et al.

(10) Patent No.: US 11,781,181 B2
(45) Date of Patent: *Oct. 10, 2023

(54) NUCLEIC ACID AMPLIFICATION DEVICE, NUCLEIC ACID AMPLIFICATION METHOD, AND CHIP FOR NUCLEIC ACID AMPLIFICATION

(71) Applicants: NATIONAL INSTITUTE OF ADVANCED INDUSTRIAL SCIENCE AND TECHNOLOGY, Tokyo (JP); Kyorin Pharmaceutical Co., Ltd., Tokyo (JP)

(72) Inventors: Hidenori Nagai, Ikeda (JP); Shunsuke Furutani, Ikeda (JP); Yoshihisa Hagihara, Ikeda (JP); Yusuke Fuchiwaki, Takamatsu (JP)

(73) Assignees: NATIONAL INSTITUTE OF ADVANCED INDUSTRIAL SCIENCE AND TECHNOLOGY, Tokyo (JP); KYORIN PHARMACEUTICAL CO., LTD., Tokyo (JP)

( * ) Notice: Subject to any disclaimer, the term of this patent is extended or adjusted under 35 U.S.C. 154(b) by 169 days.

This patent is subject to a terminal disclaimer.

(21) Appl. No.: 16/782,794

(22) Filed: Feb. 5, 2020

(65) Prior Publication Data
US 2020/0157607 A1     May 21, 2020

Related U.S. Application Data

(63) Continuation of application No. 15/322,000, filed as application No. PCT/JP2015/069549 on Jul. 7, 2015, now Pat. No. 11,098,347.

(30) Foreign Application Priority Data

Jul. 8, 2014    (JP) .................................. 2014-140758

(51) Int. Cl.
    *C12Q 1/686*      (2018.01)
    *B01L 7/00*      (2006.01)
      (Continued)

(52) U.S. Cl.
    CPC ........ *C12Q 1/686* (2013.01); *B01L 3/502715* (2013.01); *B01L 7/525* (2013.01);
      (Continued)

(58) Field of Classification Search
    CPC ..... C12Q 1/686; C12Q 1/6844; B01L 17/525; B01L 7/525; B01L 2400/04;
      (Continued)

(56) References Cited

U.S. PATENT DOCUMENTS 8,678,787 B2    3/2014   Hirata et al.
8,684,707 B2    4/2014   Kanai et al.
      (Continued)

FOREIGN PATENT DOCUMENTS

CA      2 479 452 A1    2/2005
CN      1680574 A     10/2005
      (Continued)

OTHER PUBLICATIONS

Frey et al. Autonomous microfluidic multi-channel chip for real-time PCR with integrated liquid handling. Biomed Microdevices 9:711-718. (Year: 2007).*
      (Continued)

*Primary Examiner* — Samuel C Woolwine
(74) *Attorney, Agent, or Firm* — Leydig, Voit & Mayer, Ltd.

(57) ABSTRACT

The present invention provides a reciprocal-flow-type nucleic acid amplification device comprising:
heaters capable of forming a denaturation temperature zone and an extension/annealing temperature zone;
      (Continued)

a fluorescence detector capable of detecting movement of a sample solution between the two temperature zones;

a pair of liquid delivery mechanisms that allow the sample solution to move between the two temperature zones and that are configured to be open to atmospheric pressure when liquid delivery stops; a substrate on which the chip for nucleic acid amplification according to claim 2 can be placed; and a control mechanism that controls driving of each liquid delivery mechanism by receiving an electrical signal from the fluorescence detector relating to movement of the sample solution from the control mechanism; the device being capable of performing real-time PCR by measuring fluorescence intensity for each thermal cycle.

7 Claims, 6 Drawing Sheets

Specification includes a Sequence Listing.

(51) Int. Cl.
  *C12N 15/09* (2006.01)
  *C12M 1/00* (2006.01)
  *B01L 3/00* (2006.01)
  *C12Q 1/6851* (2018.01)

(52) U.S. Cl.
  CPC ............. *C12M 1/00* (2013.01); *C12N 15/09* (2013.01); *C12Q 1/6851* (2013.01); *B01L 2300/0654* (2013.01); *B01L 2300/0883* (2013.01); *B01L 2400/0475* (2013.01); *Y02A 40/70* (2018.01)

(58) Field of Classification Search
  CPC ......... B01L 2400/0403; B01L 2400/00; B01L 2400/0445; B01L 2400/0475; B01L 2400/0487; B01L 2400/049; B01L 3/502715
  See application file for complete search history.

(56) References Cited

U.S. PATENT DOCUMENTS

| | | | |
|---|---|---|---|
| 2003/0082081 A1 | 5/2003 | Fouillet et al. | |
| 2004/0180346 A1* | 9/2004 | Anderson | A61P 35/00 435/6.1 |
| 2005/0048540 A1 | 3/2005 | Inami et al. | |
| 2005/0202489 A1 | 9/2005 | Cho et al. | |
| 2005/0255007 A1 | 11/2005 | Yamada et al. | |
| 2007/0077170 A1 | 4/2007 | Tanaami et al. | |
| 2007/0243522 A1 | 10/2007 | Sasaki et al. | |
| 2008/0220415 A1 | 9/2008 | Park et al. | |
| 2008/0247916 A1 | 10/2008 | Inaba et al. | |
| 2009/0148933 A1 | 6/2009 | Battrell et al. | |
| 2009/0162929 A1* | 6/2009 | Ikeda | B01L 7/525 435/303.1 |
| 2010/0291667 A1 | 11/2010 | Segawa et al. | |
| 2011/0076170 A1 | 3/2011 | Fujisaki et al. | |
| 2011/0189683 A1 | 8/2011 | Stroganov et al. | |
| 2011/0229898 A1 | 9/2011 | Bell et al. | |
| 2012/0052560 A1 | 3/2012 | Knight et al. | |
| 2012/0058460 A1 | 3/2012 | Coursey et al. | |
| 2012/0178091 A1* | 7/2012 | Glezer | B01L 7/525 435/6.12 |
| 2012/0258487 A1* | 10/2012 | Chang | C12N 15/1027 435/34 |
| 2013/0121880 A1 | 5/2013 | Yamazaki | |
| 2013/0288916 A1 | 10/2013 | Alexandre et al. | |
| 2014/0005066 A1 | 1/2014 | Boles et al. | |
| 2014/0045191 A1 | 2/2014 | DeJohn et al. | |
| 2015/0031087 A1* | 1/2015 | Nagai | C12Q 1/686 435/91.2 |
| 2016/0199835 A1* | 7/2016 | Tachibana | B01J 19/0093 435/303.2 |
| 2017/0130261 A1* | 5/2017 | Nagai | B01L 3/502715 |
| 2017/0130461 A1 | 5/2017 | Nagai et al. | |

FOREIGN PATENT DOCUMENTS

| | | |
|---|---|---|
| CN | 1934275 A | 3/2007 |
| CN | 103026241 A | 4/2013 |
| CN | 103608467 A | 2/2014 |
| EP | 0793098 A1 | 9/1997 |
| JP | H09-080021 A | 3/1997 |
| JP | 2002-014100 A | 1/2002 |
| JP | 2003-200041 A | 7/2003 |
| JP | 2005-065607 A | 3/2005 |
| JP | 2005-204678 A | 8/2005 |
| JP | 2005-323519 A | 11/2005 |
| JP | 2006-271216 A | 10/2006 |
| JP | 2007-101200 A | 4/2007 |
| JP | 2007-285777 A | 11/2007 |
| JP | 2008-050382 A | 3/2008 |
| JP | 2008-253227 A | 10/2008 |
| JP | 2009-030534 A | 2/2009 |
| JP | 2009-074418 A | 4/2009 |
| JP | 2009-517075 A | 4/2009 |
| JP | 2009-232700 A | 10/2009 |
| JP | 2010-284152 A | 12/2010 |
| JP | 2011-117805 A | 6/2011 |
| JP | 2012-250018 A | 12/2012 |
| JP | 2013-050108 A | 3/2013 |
| JP | 2013-055921 A | 3/2013 |
| JP | 2014-007200 A | 1/2014 |
| JP | 2014-507937 A | 4/2014 |
| WO | WO 2006/124458 A2 | 11/2006 |
| WO | WO 2007/063347 A1 | 6/2007 |
| WO | WO 2008/061129 A2 | 5/2008 |
| WO | WO 2008/069266 A1 | 6/2008 |
| WO | WO 2009/113356 A1 | 9/2009 |
| WO | WO 2009/125676 A1 | 10/2009 |
| WO | WO 2012/094459 A2 | 7/2012 |
| WO | WO 2013/132645 A1 | 9/2013 |
| WO | WO 2014/024608 A1 | 2/2014 |

OTHER PUBLICATIONS

Crews et al., "Continuous-flow thermal gradient PCR," *Biomed Microdevices*, 10(2): 187-195 (2008).

Brunklaus et al., "Fast nucleic acid amplification for integration in point-of-care applications," *Electrophoresis*, 33: 3222-3228 (2012).

Chiou et al., "A Closed-Cycle Capillary Polymerase Chain Reaction Machine," *Analytical Chemistry*, 73(9): 2018-2021 (2001).

Fuchiwaki et al., "Study of DNA Amplification Efficiency Based on Temperature Analyses of the Moving Fluid in a Liquid-Plug Flow PCR System," *Bull. Chem. Soc. Jpn.*, 84(10): 1075-1081 (2011).

Kopp et al., "Chemical Amplification: Continuous-Flow PCR on a Chip," *Science*, 280: 1046-1048 (1998).

Nara Medical University, "Development of Compact and High-speed Device for Cancer Cell Diagnosis Using Photodynamic Diagnosis and Microchannel," *Strategic Core Technology Advancement Program under Third Supplementary Budget of Fiscal Year 2011 (Heisei 23), Report on Research and Development Results, etc.* Feb. 2013 (*Heisei 25*), pp. 1-37 [publication date unknown].

Neuzil et al., "Rapid detection of viral RNA by a pocket-size real-time PCR system," *Lab Chip*, 10: 2632-2634 (2010).

Japanese Patent Office, International Search Report in International Patent Application No. PCT/JP2015/069549 (dated Oct. 6, 2015).

European Patent Office, Extended European Search Report in European Patent Application No. 15818467.1 (dated Jan. 4, 2018).

Chinese Patent Office, The First Office Action in Chinese Patent Application No. 201580036603.X (dated Aug. 2, 2018).

Japanese Patent Office, Notification of Reasons for Refusal in Japanese Patent Application No. 2017-184881 (dated Dec. 11, 2018).

European Patent Office, Communication Pursuant to Article 94(3) EPC in European Patent Application No. 15818467.1 (dated Jul. 30, 2019).

(56) References Cited

OTHER PUBLICATIONS

Hughes, "Glass: a fragile industry?," *Industrial Minerals*, Article 3183098 (Apr. 4, 2013) [obtained at https://www.indmin.com/Article/3183098/Glass-a-fragile-industry.html?ArticleId=3183098].

Fuchiwaki et al., "A Practical Liquid Plug Flow-through Polymerase Chain-Reaction System Based on a Heat-Resistant Resin Chip," *Anal. Sci.*, 27(3): 225-230 (2011).

Nagai et al., "Development of Rapid Multiplex Realtime PCR System for Pathogen Detection," *8th Bio-Related Chemistry Symposium*, Abstract (Sep. 12, 2014).

Nagai et al., "Development of Rapid Multiplex Realtime PCR System for Pathogen Detection," *8th Bio-Related Chemistry Symposium*, Presentation Slides (Sep. 12, 2014).

Japanese Patent Office, Submission of Certificate for Exception to Loss of Novelty for Japanese Patent Application No. 2011-197313 (Sep. 16, 2011).

China National Intellectual Property Administration, Office Action in Chinese Patent Application No. 201910720912.9 (dated May 25, 2022).

\* cited by examiner

NUCLEIC ACID AMPLIFICATION DEVICE, NUCLEIC ACID AMPLIFICATION METHOD, AND CHIP FOR NUCLEIC ACID AMPLIFICATION

CROSS-REFERENCE TO RELATED APPLICATIONS

This patent application is a continuation of copending U.S. patent application Ser. No. 15/322,000, filed on Dec. 23, 2016, which is the U.S. national phase of International Patent Application No. PCT/JP2015/069549, filed on Jul. 7, 2015, which claims the benefit of Japanese Patent Application No. 2014-140758, filed Jul. 8, 2014, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 3,617 bytes ASCII (Text) file named "747708SequenceListing.txt," created Feb. 4, 2020.

TECHNICAL FIELD

The present invention relates to a nucleic acid amplification device, a nucleic acid amplification method, and a chip for nucleic acid amplification.

BACKGROUND ART

The detection of nucleic acids is central in various fields, such as research and development of medicine, forensic science, clinical tests, and identification of types of agricultural products and pathogenic microorganisms. The capability to detect various diseases, such as cancer, infection of microorganisms, gene markers, etc., through molecular phylogenetic analysis is a universal technique for the diagnosis of diseases and the risk of developing diseases, the search for markers, the evaluation of food and environmental safety, the proof of crimes, and many other techniques.

One of the most powerful basic technologies for detecting a small amount of nucleic acid, which is a gene, is a method for analyzing a product obtained by exponentially replicating a part or the whole of a nucleic acid sequence.

PCR is a potent technique for selectively amplifying a specific region of DNA. With PCR, one can quickly produce millions of copies of the target DNA sequence in a template DNA from a single template DNA molecule. In PCR, a two- or three-phase temperature cycle, called a "thermal cycle," is repeated to sequentially perform the following individual reactions: denaturation of DNA into single strands; annealing of primers to the denatured DNA single strands; and extension of the primers by a thermostable DNA polymerase enzyme. This cycle is repeated until enough copies for analysis have been obtained. In principle, each cycle of PCR can double the number of copies. In reality, as the thermal cycle continues, the concentrations of required reactants are reduced, so that the buildup of amplified DNA products eventually ceases. For general details concerning PCR, see "Clinical Applications of PCR," (edited by) Dennis Lo, Humana Press (located in Totowa, N.J., 1998), and "PCR Protocols—A Guide to Methods and Applications," (edited by) M. A. Innis et al., Academic Press Inc. (located in San Diego, Calif.)(1990).

Although PCR is a potent technique for selectively amplifying the desired DNA, confirmation by gel electrophoresis, etc., is necessary to confirm the amplified DNA after the completion of PCR. Therefore, as an improved PCR method, real-time PCR evolving or quenching fluorescence in accordance with the amplified amount of the desired DNA was developed and the presence or absence of the desired DNA in a sample became easily confirmed. In conventional PCR methods, when the amount of template DNA in a sample before PCR exceeds a certain amount, the amount of amplified DNA after PCR often plateaus and the template DNA amount before PCR cannot be quantified. However, in the real-time PCR method, before PCR plateaus, the amount of amplified DNA during PCR can be detected in real-time; therefore, the amount of template DNA before PCR can be quantified from the DNA amplification state. Accordingly, the real-time PCR method is also called a quantitative PCR method.

Quantification of the target DNA amount by real-time PCR has particular clinical utility and is used, for example, for monitoring changes in viral load to confirm therapeutic effects against virus infection, such as the AIDS virus (HIV). DNA quantification by real-time PCR is also effective for the diagnosis of opportunistic infections, such as herpesvirus (HHV), with which many subjects have been subclinically infected since infancy and which develop as a result of weakened physical strength or the like.

PCR and real-time PCR are potent methods for exponentially amplifying genes by thermal cycling. General-purpose thermal cycle devices used in PCR are slow in temperature control due to the huge thermal capacity of the aluminum block used as a heater, and it conventionally takes 1 to 2 hours, or even more in some cases, to perform 30 to 40 cycles of PCR. Accordingly, even with the use of a state-of-the-art genetic testing device, analysis usually takes a total of 1 hour or more. Increasing the speed of PCR has been a great challenge since the development of this technique. Various methods have been developed for increasing the speed. Methods for increasing the speed of thermal cycling samples are classified into the following three types of methods.

In the first method, a sample solution is introduced into the device and temperature cycling is performed with time while the solution is held in the same portion (Non-patent Literature (NPL) 1 and Patent Literature (PTL) 1). This method is intended to increase the speed of thermal cycling by reducing the sample amount and thereby reducing the thermal capacity. However, there is a limit to the reduction of thermal capacity of the chamber or heater itself. Therefore, it takes at least about 30 seconds per cycle to perform sufficient amplification reactions. It takes 15 minutes or more to complete the PCR reaction even with the fastest device.

The second method is called continuous-flow PCR. In this method, a sample solution passes through a microchannel to move through multiple temperature zones spaced apart from each other while the solution is continuously fed without stopping. Among such continuous-flow PCR methods, a system of quickly controlling the sample temperature by passing a sample solution through serpentine microchannels above three heaters controlled at constant temperatures is known (NPL 2). Since this continuous flow PCR method does not require temperature changes of external devices, such as containers and heaters, the fastest temperature control can be theoretically expected. In an extremely fast case, amplification of DNA is effectuated in about 7 minutes. However, to perform quantitative real-time PCR by using continuous-flow PCR, a mechanism that enables fluorescence observation of the whole region of the serpentine microchannels or 30 to 50 regions of each serpentine microchannel in the same temperature zone is necessary. Specifically, an excitation light source that can uniformly irradiate a wide region and a high-sensitivity video camera or a line scanner for fluorescence observation is necessary, which unavoidably results in a large and expensive system structure.

In the third method, like the second method, multiple temperature zones spaced apart from each other are connected by microchannel(s), and a sample solution is reciprocally moved through the same microchannel(s) in such a manner that the sample solution is stopped in each temperature zone for a certain period of time, and heated (Patent Literature (PTL) 2). This method is advantageous in that the time of contacting a sample with each temperature zone can be freely set to perform thermal cycling. However, in order to introduce a sample and pump it to these temperature zones reciprocally or rotationally, many integrated valves and pumps, as well as detectors for observing the position of the sample solution, are necessary to inhibit the sample solution from unwillingly moving from a desirable temperature zone position in the microchannel due to the expansion of tiny air bubbles generated in the sample heated at a high temperature side and/or a difference in vapor pressure generated on the gas-liquid interface when the sample solution moves through a microchannel having a temperature gradient of from about 95° C. or more for a denaturation reaction to about 60° C. for an annealing reaction, and device miniaturization was difficult (NPL 3 and 4 and PTL 3).

The market for genetic testing using PCR/real-time PCR devices is favorably growing. In particular, genetic testing for infectious diseases, such as viral hepatitis, sexually transmitted diseases, and influenza, is also rapidly spreading in Japan. The usefulness of genetic testing for cancer treatment has become apparent. For example, EGFR gene mutation can be used as a rule of thumb for applying the cancer agent Iressa. Therefore, genetic testing for the EGFR gene, K-ras gene, EWS-Flil gene, TLS-CHOP gene, SVT-SSX gene, and c-kit gene in lung cancer, pancreatic cancer, etc., has recently been covered by insurance.

In PCR, primers are attached to a template DNA and the target DNA located between the primer sequences is specifically detected by a DNA polymerase. Although PCR can be used for detecting DNA, PCR cannot directly detect RNA. Accordingly, in order to detect RNA viruses, such as influenza viruses or noroviruses, PCR is performed after complementary cDNA is synthesized by reverse transcriptase using RNA as a template; that is, so-called RT-PCR is performed. Thus, substantially a two-stage step must be performed. Furthermore, PCR and RT-PCR need a rapid temperature rise and fall and thus require a special incubator. Therefore, there is a problem in that the adaptation of PCR and RT-PCR to automation is not easy.

In recent years, multiplex PCR, which simultaneously amplifies multiple genetic regions by using multiple pairs of primers in one PCR system, has been attracting attention. Real-time multiplex PCR, which was developed from a multiplex PCR, is intended to individually detect and quantify multiple different target genes with less influence (cross-talk) of other target genes and without compromising sensitivity. However, it has been reported that two or more quantitative multiplex reactions are often difficult due to the problem of overlapping wavelengths and kinds of labelable fluorescent substances.

At present, genetic testing is taken to and performed at laboratories or analysis centers. However, if a high-speed, real-time PCR device that can quickly perform genetic testing on the spot is available, the course of treatment and countermeasure can be determined on the spot. Therefore, such a device is considered to be an epoch-making technique that can replace current genetic testing equipment. In particular, as a quarantine measure to prevent pandemics of foot-and-mouth disease, highly pathogenic influenza, and the like, quick and correct judgment on the spot and prevention of spreading of secondary infection are important. The need for such a high-speed, real-time PCR device is tremendous.

In particular, to realize a service that allows genetic testing to be immediately performed in a clinical setting or on the spot where an infectious disease occurs, a high-speed and highly portable real-time PCR device that can operate at low cost is necessary.

CITATION LIST

Patent Literature

PTL 1: Canadian Patent Application Publication No. 2479452
PTL 2: JP2003-200041A
PTL 3: WO2006/124458

Non-Patent Literature

NPL 1: Neuzil et al. (Lab Chip 10:2632-2634 (2010))
NPL 2: Kopp et al. (Science 280: 1046-1048 (1998))
NPL 3: Chiou et al. (Anal Chem 73: 2018-2021 (2001))
NPL 4: Brunklaus et al. (Electrophoresis 33: 3222-3228 (2012))

SUMMARY OF INVENTION

Technical Problem

An object of the present invention is to provide a small, nucleic acid amplification device that can be carried for use on the spot and that can perform high-speed, real-time PCR, a plate for the device, and a nucleic acid amplification method.

Solution to Problem

To achieve an increased reaction efficiency and provide a smaller amplification device, the present invention provides a reciprocal-flow-type, high-speed, real-time, nucleic acid amplification device that comprises: two temperature zones disposed on a flat surface; a microchannel contacted to each temperature zone, both ends of the microchannel being configured to be open to atmospheric pressure when blowers, fans, etc. are stopped; and liquid delivery mechanisms by which a plug sample solution is reciprocated between precise positions in the temperature zones through the microchannel to perform thermal cycling while simultaneously confirming the passing of the PCR solution and measuring fluorescence intensity for each thermal cycle. In another exemplary embodiment, the nucleic acid amplification method comprises converting RNA to cDNA by reverse transcription and subjecting the cDNA to PCR.

Specifically, the present invention provides the following nucleic acid amplification devices, nucleic acid amplification methods, and chips.

(1) A reciprocal-flow-type nucleic acid amplification device comprising:

heaters capable of forming a denaturation temperature zone and an extension/annealing temperature zone;

a fluorescence detector capable of detecting movement of a sample solution between the two temperature zones;

a pair of liquid delivery mechanisms that allow the sample solution to move between the two temperature zones and that are configured to be open to atmospheric pressure when liquid delivery stops;

a substrate on which a chip for nucleic acid amplification can be placed; and a control mechanism that controls driving of each liquid delivery mechanism by receiving an electrical signal relating to movement of the sample solution from the fluorescence detector, the device being capable of performing real-time PCR by measuring fluorescence intensity for each thermal cycle.

(2) A chip for nucleic acid amplification comprising at least one microchannel, the microchannel comprising:

curved-microchannels each for the denaturation temperature zone and the extension/annealing temperature zone of the nucleic acid amplification device according to (1);

a linear intermediate-microchannel connecting the curved-microchannels; and connections at both ends of the microchannel, the connections being connectable to the liquid delivery mechanisms of the nucleic acid amplification device according to (1).

(3) The nucleic acid amplification device according to (1), wherein the liquid delivery mechanisms are microblowers or fans.

(4) A nucleic acid amplification method comprising the following steps:

step 1: placing the chip for nucleic acid amplification according to (2) on the substrate according to (1) in such a manner that the denaturation temperature zone includes one curved-microchannel and the extension/annealing temperature zone includes another curved-microchannel;

step 2: introducing a sample solution into the microchannel;

step 3: connecting a pair of liquid delivery mechanisms to liquid delivery mechanism connections at both ends of the microchannel; and step 4: reciprocating the sample solution between the two curved-microchannels of the microchannel by the liquid delivery mechanisms to perform thermal cycling, and simultaneously measuring the fluorescence intensity of the sample solution and confirming the passing of the sample solution for each thermal cycle using at least one fluorescence detector in the intermediate-microchannel to perform real-time PCR.

(5) The nucleic acid amplification method according to (4), wherein the measurement of fluorescence intensity is performed by simultaneously measuring two or more fluorescent wavelengths to simultaneously measuring real-time PCR of multiple genes in one microchannel.

(6) The nucleic acid amplification method according to (4) or (5), wherein the measurement of fluorescence intensity is performed using a calibration curve obtained from the number of cycles Ct derived from a fluorescence intensity matrix per thermal cycle (a two-dimensional array of an amplification curve).

(7) The nucleic acid amplification method according to any one of (4) to (6), wherein the nucleic acid amplification method is selected from the group consisting of polymerase chain reaction (PCR), reverse transcription PCR (RT-PCR), multiplex PCR, multiplex RT-PCR, real-time PCR, and real-time RT-PCR.

(8) The nucleic acid amplification method according to any one of (4) to (7), comprising performing interruption analysis, which is made possible by forming two or more microchannels on a flat substrate in such a manner that the operation of liquid delivery through each of the microchannels can be independently controlled.

(9) The nucleic acid amplification method according to any one of (4) to (8), the method comprising:

connecting an end of a filtered pipette tip of a micropipette to one of the connections so as to introduce a sample solution into the microchannel;

removing the micropipette with the pipette tip being connected to the connection, and then connecting the pipette tip to one of the liquid delivery mechanisms.

(10) The nucleic acid amplification method according to any one of (4) to (9), wherein the volume of the sample solution introduced into the microchannel is in the range of 5 µL to 50 µL.

(11) The chip for nucleic acid amplification according to (2), the chip being for use in the nucleic acid amplification method according to any one of (4) to (10).

Advantageous Effects of Invention

According to the present invention, since two liquid delivery mechanisms (preferably fans) and one fluorescence detector are provided for each microchannel, a low-cost and compact portable device can be realized.

Furthermore, since the sample solution is reciprocated between two temperature zones, faster real-time PCR can be achieved by simultaneously and quickly performing the confirmation of passing of the PCR solution and the measurement of fluorescence intensity for each thermal cycle.

In conventional methods using thermal cycling by reciprocating a sample solution, a pressure source, such as a syringe pump, is connected to a microchannel, and a plug-like sample solution is reciprocated by repeating pressurization and depressurization. In this process, the inside of the microchannel at the side connected to such a pressure source must be a closed system so as not to leak pressure from the plug-like sample solution in the microchannel. When the force of the plug-like sample solution applied to the gas-liquid interface, which is generated by applying or reducing pressure by means of the pressure source, exceeds the static friction between the plug-like sample solution and the microchannel internal wall, liquid delivery begins. On the other hand, when pressurization or depressurization is stopped to stop the plug-like sample solution, the pressure of the sample solution acting on the gas-liquid interface remains inside the closed microchannel at the pressure source side, and the solution keeps moving for a while until the energy is completely consumed by kinetic friction and then stops. In particular, when the sample solution is heated to about 95° C. or higher for a denaturation reaction as in PCR, the influence of changes in the internal pressure of the sample solution, such as viscosity changes and the formation of tiny air bubbles, is great and the amount of movement after stopping the pressure source, such as a pump, varies widely. To stop the sample solution at a precise position, several measures, such as dedicated valves for releasing the internal pressure of the microchannel as well as complicated operation of the pressure source, and dedicated sensors for confirming the position of the solution, were necessary.

In contrast, although the present invention utilizes applying or reducing pressure in the microchannel by blowing air using blowers, fans, etc., to reciprocate a plug-like sample solution, liquid delivery stops immediately after air blowing using the blowers, fans, etc., is stopped, when or immediately before the solution has reached the precise position on each temperature zone. This is because when air blowing is stopped, the internal pressure of the microchannel is instantaneously open to atmospheric pressure and the pressure acting on the plug-like sample solution is lost, whereby liquid delivery stops immediately. Accordingly, even in the absence of multiple valves for releasing pressure for controlling the position of the sample solution, a precise position control can be achieved by confirming the passing of the sample solution only at one point located between each temperature zone. Furthermore, since fluorometry can also be simultaneously performed at the point where the position of the reciprocated liquid is confirmed for each cycle, a real-time PCR thermal cycler with the simplest structure where only one point in the linear microchannel is used as a detecting point can be realized.

In the present invention, a polymerase chain reaction, commonly referred to as PCR, is used. PCR uses multiple cycles of denaturation, annealing of primer pairs to opposite strands, and primer extension to exponentially increase the number of copies of a target nucleic acid sequence. In its variation, called reverse transcription PCR (RT-PCR), reverse transcriptase (RT) is used to make a complementary DNA (cDNA) from mRNA, and the cDNA is then amplified by PCR to produce a large number of copies of DNA.

As an RT-PCR reaction, one-step RT-PCR can also be used. One-step RT-PCR is an RT-PCR method capable of performing RT-PCR quickly and conveniently in one step from the incubation in RT to cycling in PCR without opening and closing the tube or adding a reagent. In this technical field, various kits and protocols for one-step RT-PCR (such as One Step RT-PCR Mix of QIAGEN) can be used and appropriately selected to perform one-step RT-PCR.

For various other permutations of PCR, see, for example, U.S. Pat. Nos. 4,683,195, 4,683,202 and 4,800,159; Mullis et al, Meth. Enzymol. 155: 335 (1987); and Murakawa et al, DNA 7: 287 (1988), each of which is herein incorporated in its entirety by reference.

DESCRIPTION OF EMBODIMENTS

One embodiment of the reactor of the present invention is explained below with reference to FIGS. 1 to 9.

Figure 1:
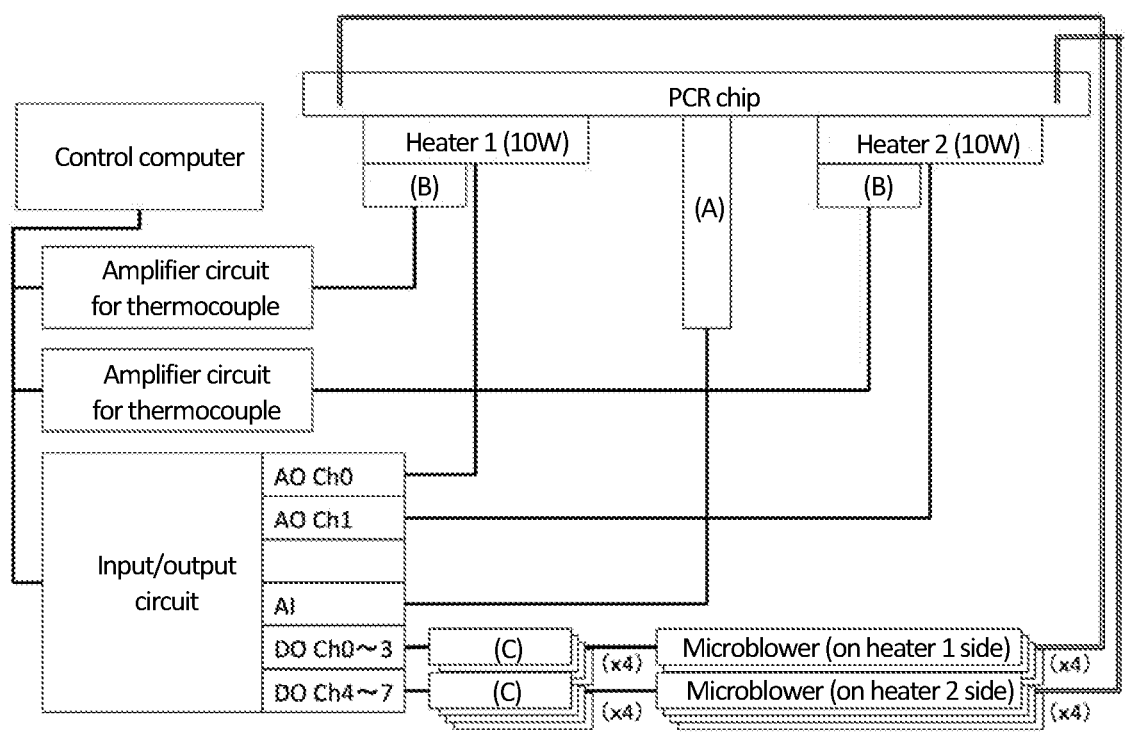
FIG. 1 shows the configuration of a nucleic acid amplification device.

As shown in FIG. 1, the device used in high-speed, real-time PCR is configured to comprise a substrate for placing a PCR chip thereon (not shown), a temperature control section for a PCR chip, liquid delivery microblowers as liquid delivery mechanisms, a fluorescence detector, a control computer as a control mechanism, and a battery for power supply.

The temperature control section for a PCR chip is configured to comprise two cartridge heaters disposed in parallel with an interval of 10 mm therebetween so as to be in contact with the sealing surface side of the serpentine microchannels of a PCR chip without any space therebetween. To control the temperatures of the two heaters, each heater comprises a K-type thermocouple joined thereto.

A cartridge heater 1 is controlled by means of a control computer to a temperature necessary for a DNA denaturation reaction essential for PCR. The temperature (denaturation temperature zone) is preferably 90 to 100° C., and particularly preferably 95° C. A cartridge heater 2 is controlled to a temperature necessary for an annealing reaction and an extension reaction of DNA (an extension/annealing temperature zone) by a control computer. This temperature is preferably 40 to 75° C., and particularly 55 to 65° C. The temperature zone for DNA denaturation reaction and the temperature zone for annealing reaction and extension reaction are preferably controlled at constant temperatures. For example, the temperature zones are retained at constant temperatures by PID (proportion-integration-differential) control.

The PCR solution to be delivered is quantified using a micropipette or the like to the required amount within the range of 5 to 50 μL, and more preferably 5 to 25 μL. With the PCR sample solution being contained in the micropipette, the disposable tip of the micropipette is mounted on one end of a microchannel. After the micropipette body is removed, an air pressure tube connected to a liquid delivery microblower is connected instead and pressure is applied by blowing air, so that a sample solution can be fed into the microchannel of the PCR chip.

The PCR sample solution is a premixed product of components necessary for PCR with a fluorescent probe, such as TaqMan probe, Cycleave probe, or E Probe®, and a fluorescent dye, such as SYBR GREEN, so as to enable real-time PCR. As such fluorescent probes, reagent kits for real-time PCR and products synthesized by an outsourcing company can be used.

The fluorescence detector is disposed to measure the fluorescence intensity at one detecting point on a linear microchannel that is disposed at the center of each microchannel. When the PCR solution delivered from one of the serpentine microchannels by applying pressure passes through a detecting point, liquid delivery microblowers are stopped, so that the PCR solution can be retained in the other serpentine microchannel for a certain period of time.

The control computer can be programmed to simultaneously control two microblowers connected to each microchannel. While continuously monitoring the fluorescence intensity at a detecting point at the center of each microchannel, the microblowers are alternately switched to alternately move the PCR sample solution to each serpentine microchannel above each heater for a predetermined period of time and perform thermal cycling. Further, in the real-time PCR method, the control computer simultaneously records changes in fluorescence intensity per cycle, which increases as the target DNA is amplified by thermal cycling in the real-time PCR method, and calculates the number of cycles (Ct value) in which the fluorescence intensity crosses a certain threshold, thus quantifying the initial amount of target DNA.

The PCR chip for use in high-speed, real-time PCR (chip for nucleic acid amplification) is configured to comprise a COP resin substrate, which comprises four microchannels formed in parallel by injection molding, and a polyolefin transparent seal applied to the substrate.

Figure 2:
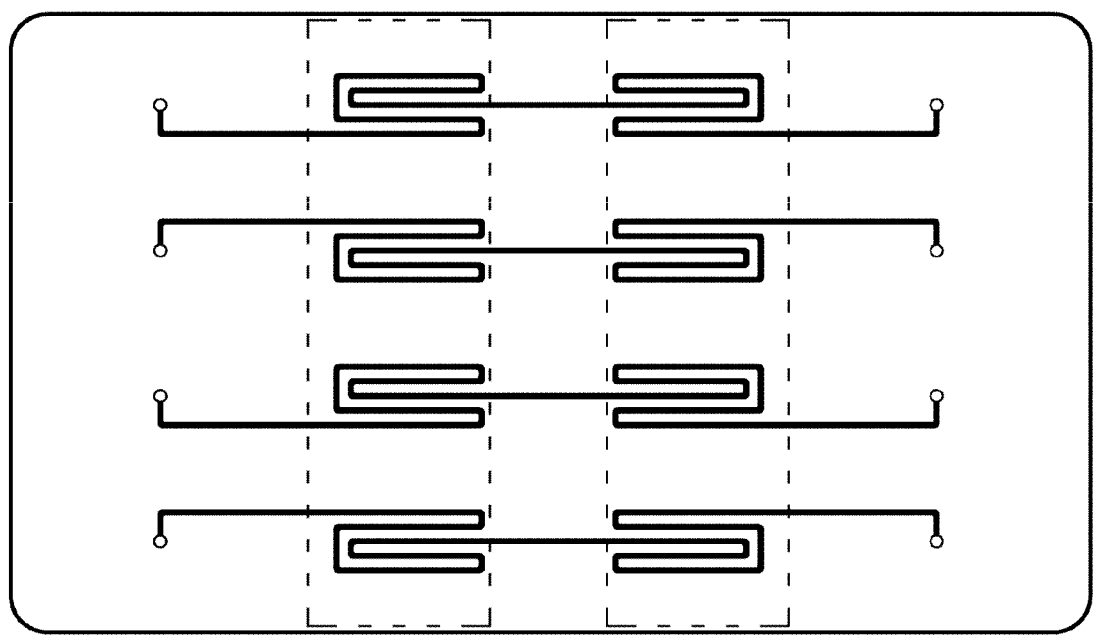
FIG. 2 shows the configuration of a PCR chip.

Each microchannel is configured to meander and turn back in two sections with a width as shown in FIG. 2 and a depth of 700 µm. Each serpentine microchannel is turned back four times in such a manner that the linear microchannel at the center of each microchannel is sandwiched between the serpentine microchannels, and at least 25 µL of the solution can be accommodated in each serpentine microchannel portion alone.

The regions encompassed by dotted lines (a denaturation temperature zone and an extension/annealing temperature zone) in FIG. 2 were heated by heaters for thermal cycling in real-time PCR.

Both ends of the microchannel are individually connected to apertures penetrating a resin substrate (connections to liquid delivery mechanisms). Even after the entire microchannel-side surface of the resin substrate is joined by a polyolefin transparent seal, the reaction solution and air can pass through the apertures into each microchannel.

The aperture is configured to permit the mounting of a disposable tip for micropipettes generally used in biochemistry experiments. After 5 to 25 µL of a PCR solution is measured, the disposable tip is directly connected, whereby the PCR solution can be introduced without the necessity of using a special instrument and without contamination, etc.

An interruption analysis is made possible by forming two or more microchannels on a flat substrate or disposing in parallel two or more flat substrates each comprising a microchannel, so that the operation of liquid delivery through each of the microchannels can be independently controlled.

The microchannel preferably comprises a material that has relatively high thermal conductivity, is stable in the temperature range necessary for PCR, is resistant to erosion by electrolytic solutions and organic solvents, and does not absorb nucleic acids or proteins. Examples of materials include glass, quartz, silicon, and various plastics. The shape of the microchannel that is in contact with multiple temperature zones may be not only a linear microchannel but also a curved microchannel, such as a serpentine microchannel having a loop shape, or a spiral microchannel. The width or depth of the microchannel does not have to be constant and the microchannel may have a partially different width or depth.

The detection of the passing of the sample solution through the microchannel into a different temperature zone and the measurement of fluorescence intensity for each thermal cycle are preferably performed using the same fluorescence detector, but may be performed using different fluorescence detectors. The method for detecting the passing of the sample solution between the temperature zones is not limited to fluorescence detection and may be an optical methodology, such as colorimetry and optical absorption, or electric methods utilizing, for example, changes in capacitance or including electrochemical reactions. Two or more temperature zones in contact with the microchannel may be in contact from the outside of the microchannel or may be included inside the microchannel.

In the microchannel shown in FIG. 2, two serpentine microchannels for a denaturation temperature zone and an extension/annealing temperature zone are connected to each other via a linear intermediate-microchannel, and the passing of the sample solution and fluorescence are detected in the internal microchannel. In FIG. 2, an intermediate-microchannel is disposed along a straight line connecting two apertures (connections to liquid delivery mechanisms), and the passing of the test solution and fluorescence are detected in the intermediate-microchannel. Accordingly, even if the PCR chip (chip for nucleic acid amplification) is turned upside down (turned 180 degrees) and disposed on the substrate, fluorescence can be detected using a fluorescence detector.

For example, as shown in FIG. 2, a PCR chip may be fixed to the two heaters in such a manner that the sealing surface of each serpentine microchannel portion encompassed by a dotted line is attached, and, after use, the PCR chip may be removed, disposed, and replaced for the intended use. Two liquid delivery microblowers are used for each microchannel of the PCR chip. Each of the microblowers is connected via an air pressure tube to disposable tips connected to both ends of the microchannel. The microblowers are operated alternately, thus enabling bi-directional delivery of a liquid. It is also possible to simultaneously subject different samples to thermal cycling, for example, to perform multiple PCR, by increasing the number of liquid delivery microblowers in accordance with the number of microchannels.

The term "multiplex PCR" in the context of the present invention refers to PCR using a primer set comprising two or more types of forward and reverse primers in a single reaction solution. The term "primer set" in the context of the present invention refers to a combination of one type or two or more types of forward primers and reverse primers. In the present invention, a primer set comprising even only one type of reverse primer can also be used as a primer set for multiplex PCR as long as different amplification products are produced by using the reverse primer in combination with two or more types of forward primers (as primer pairs).

In the multiplex PCR of the present invention, fluorescence intensities are simultaneously measured to detect amplification of the target genes corresponding to different fluorescence wavelengths. Although detection can be performed using multiple fluorescence detectors, detection is feasible even using one wavelength of light.

The present invention is described below more specifically with reference to Examples. However, the present invention is not limited to the Examples.

Example 1: Quantification of *Escherichia coli*

Using a PCR chip for high-speed, real-time PCR and the device of the present invention, *Escherichia coli* (*E. coli*) was quantified.

*Escherichia coli* (DH5α strain) was cultured overnight in a Lecithin bouillon liquid medium. After an *Escherichia coli* suspension in a concentration of 1×10$^4$ cfu/μL was prepared based on the colony count by an agar plate medium assay, a series of 10-fold dilutions was made and used as a standard sample for quantitative identification.

The target DNA amplified in real-time PCR was a 106 bp DNA sequence of *Escherichia coli*-specific uid A gene (Accession Number: NC_000913.3). Using 5'-GTG TGA TAT CTA CCC GCT TCG C-3' (SEQ ID NO: 1) as a forward primer for PCR and using 5'-AGA ACG GTT TGT GGT TAA TCA GGA-3' (SEQ ID NO: 2) as a reverse primer, the final concentration of each primer in the PCR solution was adjusted to 300 nM. The sequence of TaqMan® probe for real-time PCR was 5'-FAM-TCG GCA TCC GGT CAG TGG CAG T-MGB-3' (SEQ ID NO: 3). The final concentration of the probe in the PCR solution was adjusted to 200 nM.

As another reagent, SpeedSTAR® HS DNA polymerase of Takara Bio, Inc. was used in a final concentration of 0.1 U/μL. FAST Buffer I and dNTP Mixture included in the product package were mixed in a concentration in accordance with a product manual and used as a premixture for PCR. After 0.5 μL of an *Escherichia coli* suspension in various concentrations was mixed with 12 μL of the premixture for PCR using a micropipette, the end of a disposable tip of the micropipette having a PCR solution absorbed therein was inserted into an aperture at first end of the microchannel of the PCR chip and the disposable tip and the micropipette were released. Another empty disposable tip for the micropipette was mounted on a second end of the microchannel on the first end of which the disposable tip for the micropipette containing the PCR solution has been mounted. Tubes of liquid delivery microbrewers were connected to the disposable tips. As thermal cycling conditions in high-speed, real-time PCR, a process comprising heating at 98° C. for 30 seconds for the hot-starting of DNA polymerase, further heating at 98° C. for 2 seconds and then heating at 58° C. for 4 seconds was set to be repeated for 45 cycles. High-speed, real-time PCR was performed by program control of liquid delivery microblowers.

Figure 3:
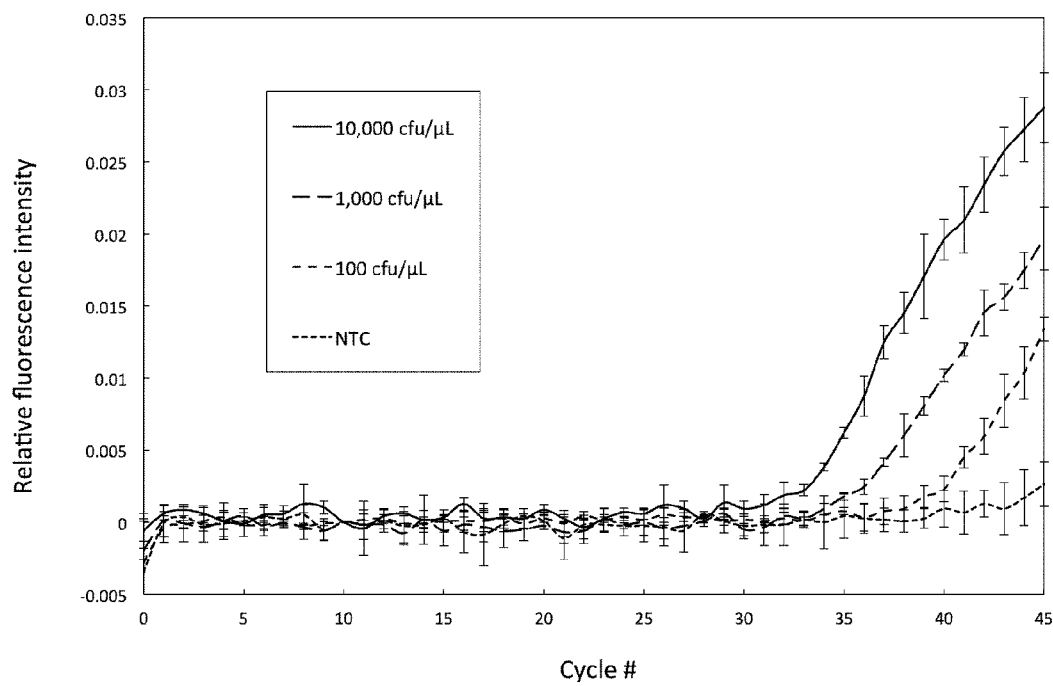
FIG. 3 shows amplification of nucleic acids in high-speed, real-time PCR.

As shown in FIG. 3, fluorescence intensity per cycle in high-speed, real-time PCR drew a sigmoid curve similar to that obtained by using a known real-time PCR device. The fluorescence amplification rate varied depending on the initial concentration of *E. coli*.

Figure 4:
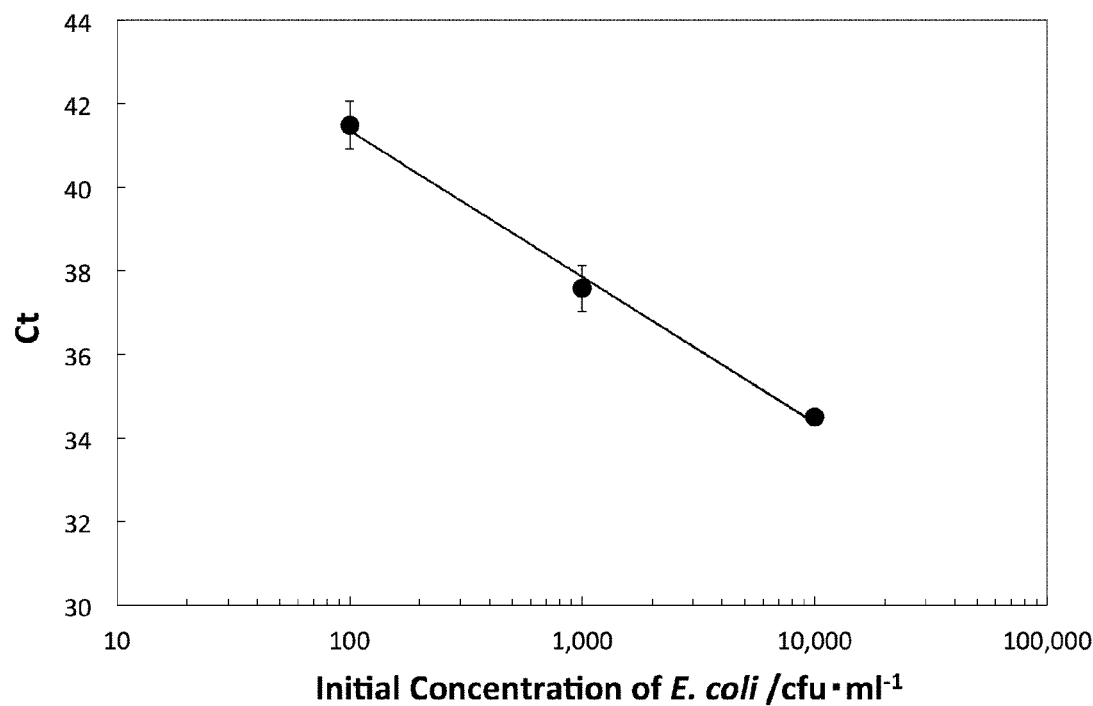
FIG. 4 shows a calibration curve of *Escherichia coli* (*E. coli*) for use in high-speed, real-time PCR.

When the number of cycles that crosses the desired threshold of fluorescence intensity was defined as Ct and a calibration curve was plotted against the initial concentration of *E. coli*, a good linearity was obtained, as shown in FIG. 4. Since the Ct value of the no template control (NTC), which is 0 cfu/μL, was 45 cycles or more, the results confirmed that quantification is feasible even at a concentration of 100 cfu/μL. The detection sensitivity was confirmed to be equivalent to that of existing real-time PCR devices.

The high-speed, real-time PCR processing time was 6 minutes and 40 seconds per 45 cycles. In contrast, the PCR processing time of even a high-speed thermal cycling device among existing commercially available devices is 45 minutes per 45 cycles. The present invention thus achieved a high-speed, real-time PCR capable of quantifying a microorganism or DNA at an extremely high speed.

Example 2: Examination of Conditions for High-Speed PCR Amplification

High-speed, real-time PCR was performed by repeating three steps consisting of a DNA denaturation reaction, an annealing reaction, and an extension reaction in which each primer is extended from the 3'-end for replication by a DNA polymerase in accordance with a DNA template sequence. Among these, the DNA denaturation reaction and the annealing reaction do not depend on the length of the target DNA and are completed in a short time. However, the extension reaction requires time depending on the length of the target DNA and enzyme activity of the DNA polymerase used. An appropriate time setting for thermal cycling is also necessary in high-speed, real-time PCR.

10$^4$ copies of 16S ribosomal RNA gene (Accession Number KC_768803.1) of *E. coli* (DH5α strain) were used as template DNA. Changing the length of the target DNA in the range of about 200 to 800 bp among the obtained template DNA, 45 cycles of high-speed, real-time PCR were performed.

5'-GTT TGA TCC TGG CTC A-3' (SEQ ID NO: 4) was used as a common forward primer sequence and 5'-FAM-CGG GTG AGT AAT GTC TGG-TAMRA-3' (SEQ ID NO: 5) was used as a common TaqMan® probe. The following reverse primers were used in combination therewith depending on the length of the target DNA. The reverse primer sequence for a target DNA length of about 200 bp was 5'-CTT TGG TCT TGC GAC G-3' (SEQ ID NO: 6). The reverse primer sequence for about 400 bp target DNA was 5'-GCA TGG CTG CAT CAG-3' (SEQ ID NO: 7). The reverse primer sequence for about 600-bp target DNA was 5'-CTG ACT TAA CAA ACC GC-3' (SEQ ID NO: 8); and a reverse primer sequence for about 800-bp target DNA was 5'-TAC CAG GGT ATC TAA TCC-3' (SEQ ID NO: 9). The Tm values were all set to about 50° C.

Figure 5:
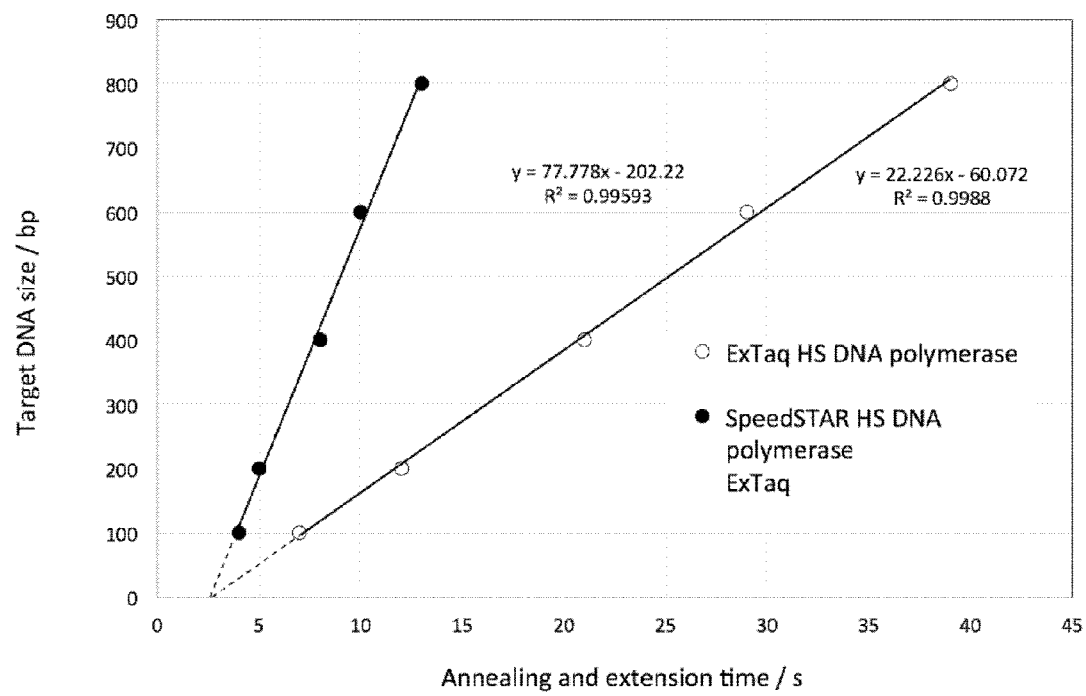
FIG. 5 shows retention time plotted against each target DNA length, the retention time allowing sufficient amplification of target DNA without exhibiting any changes in Ct values even when annealing time and extension reaction time are shortened.

FIG. 5 is a graph plotting retention time against each target DNA length, the retention time allowing sufficient amplification of target DNA without exhibiting any changes in Ct values even when the annealing time and extension reaction time are shortened. For about 100-bp short target DNA, the results of the above-mentioned uid A gene were used and plotted on the same graph. FIG. 5 shows that even when the length of the target DNA is the same, the annealing reaction time and extension reaction time vary depending on the activity of the DNA polymerase used. When the SpeedSTAR® HS DNA polymerase was used, the extension rate was about 78 bp per second. When ExTaq HS DNA polymerase was used, the extension rate was about 22 bp per second.

Theoretically, when the length of the target DNA was 0 bp, which corresponds to the X-intercept in FIG. 5, the annealing reaction time excluding the extension reaction was about 2.7 seconds, regardless of the kind of DNA polymerase. This result is consistent with the above-described previous finding.

Accordingly, theoretically, the highest-speed, real-time PCR can be performed by setting the time based on FIG. 5 in accordance with the length of the target DNA.

Example 3: Multiplex PCR High-Speed, Real-Time PCR

As an application example of high-speed, real-time PCR to a multiplex PCR method for confirming the presence or absence of multiple target DNAs from the same sample, simultaneous detection of *Neisseria gonorrhoeae*, *Chlamydia trachomatis*, and human-leukocyte-derived β actin gene was examined using a multicolor fluorescence detector that can simultaneously detect three kinds of fluorescence.

A multicolor fluorescence detector is capable of coaxially quantifying each fluorescence of blue excitation, green excitation, and red excitation. The detector can individually detect fluorescence amplification by 3 kinds of fluorescent probes, i.e., a FAM-labeled probe, a Texas red-labeled probe, and a Cy5-labeled probe at the same detecting point of a microchannel on the PCR chip. Even when a multicolor fluorescence detector is used, the detector is disposed in such a manner that 3 types of fluorescence intensity can be simultaneously detected at one detecting point on a linear microchannel located at the center of the microchannel. When the PCR solution delivered from one serpentine microchannel portion by applying pressure has passed through the detecting point, liquid delivery microblowers are stopped, so that the PCR solution can be retained in the other serpentine microchannel for a certain period of time.

The length of the target DNA for each of *Neisseria gonorrhoeae*, *Chlamydia trachomatis*, and β actin gene, and the Tm values of each of the primers and fluorescent probes were unified so as not to make a difference in amplification efficiency.

As fluorescent probes for *Neisseria gonorrhoeae*, *Chlamydia trachomatis*, and β actin gene, Texas red-, Cy5-, and FAM-labeled TaqMan® probes were used, and the final concentration of each probe in the PCR solution was adjusted to 200 nM.

The final concentration of each of three kinds of forward primers and reverse primers for *Neisseria gonorrhoeae*, *Chlamydia trachomatis*, and β actin gene in the PCR solution was adjusted to 300 nM. As another reagent, SpeedSTAR® HS DNA Polymerase produced by Takara Bio, Inc. was used in a final concentration of 0.2 U/μL, and FAST Buffer I and dNTP Mixture included in the polymerase kit were mixed in the concentrations specified by the manual to form a premixture for PCR.

As template DNAs for *Neisseria gonorrhoeae*, *Chlamydia trachomatis*, and β actin, synthetic plasmids comprising each target DNA sequence were prepared. 4 ng/μL of each plasmid was used in positive controls. Sterile water was mixed instead of plasmid in NTC. A high-speed, real-time PCR was thus performed. The thermal cycling conditions were such that after heating at 96° C. for 20 seconds for hot-starting, heating at 96° C. for 3 seconds and heating at 60° C. for 8 seconds were performed, and this process was repeated for 45 cycles. The thermal cycling time for 45 cycles under these conditions was 9 minutes and 40 seconds.

Figure 6:
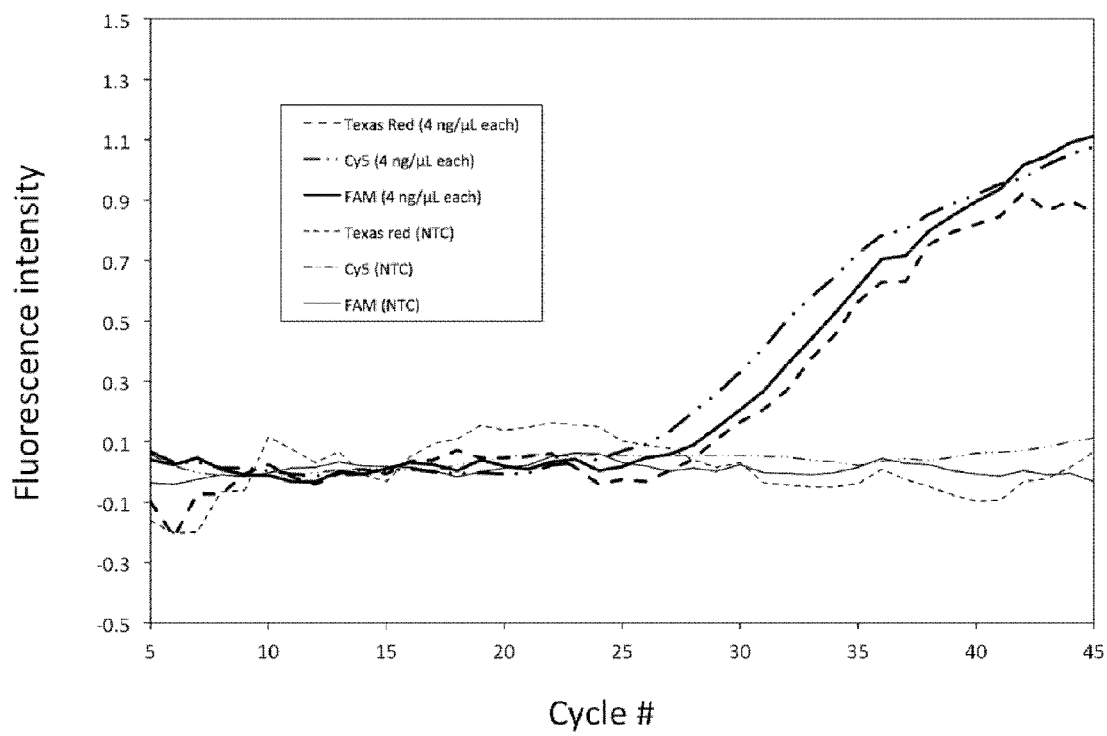
FIG. 6 shows multiplex PCRs of pathogenic microorganisms A and B and β actin gene.

FIG. 6 shows the results of multiplex PCR for *Neisseria gonorrhoeae*, *Chlamydia trachomatis*, and β actin gene using high-speed, real-time PCR. Since the sensitivity of a multicolor fluorescence detector to three fluorescent dyes varies, the results obtained by dynamic range correction are shown. In FIG. 6, the three thicker lines show changes in fluorescence intensities for three kinds of fluorescence when all template DNA were included. Compared with fluorescent signals in NTC, which are indicated by thinner lines, clear amplification was obtained and multiple-item simultaneous measurement from the same sample was achieved.

In this Example, three fluorescence intensities were simultaneously measured to detect the amplification of the target genes corresponding to each fluorescence wavelength. If liquid delivery microblowers are stopped immediately after the PCR solution delivered from one serpentine microchannel by applying pressure has passed through the detecting point and the passing of the solution is detected, it is not necessary to use all of the fluorescence detectors, and the detection is feasible even with a detection signal using one wavelength of light.

Example 4: One-Step Reverse Transcription Real-Time PCR

A technique in which a reverse transcription reaction from RNA and a real-time PCR method are conveniently performed using a single reaction solution, which is prepared by mixing a reverse transcriptase with a PCR solution beforehand, is called a one-step reverse transcription real-time PCR method. This method has been used for detecting RNA viruses, such as influenza viruses and noroviruses. In the one-step reverse transcription real-time PCR method, two-stage steps as in a general RT-PCR method are combined into one to remarkably simplify the operation. However, this method has a problem in that reverse transcriptase of the reverse transcription reaction and DNA polymerase of the real-time PCR method interfere with each other, thus resulting in poor PCR efficiency. However, quick shifting to the optimum temperatures for the activity of reverse transcriptase and DNA polymerase by high-speed temperature control allows the reverse transcription reaction and the real-time PCR method to be performed efficiently in order, thus effectuating a highly efficient one-step reverse transcription real-time PCR method. Using the PCR chip for high-speed, real-time PCR and the device of the present invention, quantification of norovirus G1 gene and G2 gene by a one-step reverse transcription real-time PCR method was actually examined.

As RNA comprising a target G1 gene or G2 gene sequence, a standard product included in a commercially available TaKaRa qPCR Norovirus (GI/GII) Typing Kit, or RNA, which is a transcription product of synthetic DNA, was used. A dilution series of the RNA was prepared using an RNase-free sterile water.

The sequences disclosed in the method for detecting noroviruses provided by the Infectious Disease Surveillance Center, National Institute of Infectious Diseases, Japan were used as the primer and probe sequences. For the norovirus G1 gene, the forward primer sequence was 5'-CGY TGG ATG CGN TTY CAT GA-3' of COG-1F (SEQ ID NO: 10); the TaqMan® probe sequences were 5'-AGA TYG CGA TCY CCT GTC CA-3' of RING1-TP (a) (SEQ ID NO: 11) and 5'-AGA TCG CGG TCT CCT GTC CA-3' of RING1-TP (b) (SEQ ID NO: 12); and the reverse primer sequence was 5'-CTT AGA CGC CAT CAT CAT TYA C-3' (SEQ ID NO: 13). For the norovirus G2 gene, the forward primer sequence was 5'-CAR GAR BCN ATG TTY AGR TGG ATG AG-3' of COG-2F (SEQ ID NO: 14); the TaqMan® probe sequence was 5'-TGG GAG GGS GAT CGC RAT CT-3' of RING2 AL_TP (SEQ ID NO: 15); and the reverse primer sequence was 5'-TCG ACG CCA TCT TCA TTC ACA-3' (SEQ ID NO: 16) of COG-2R.

As fluorescent probes for G1 gene and G2 gene, FAM-labeled TaqMan® probes were used. The final concentration of each probe in the PCR solution was adjusted to 200 nM.

The final concentrations of the forward primer and reverse primer for the G1 gene or G2 gene in the PCR solution were adjusted to 300 nM. For other reagents, PrimeScrip® Reverse Transcriptase of Takara Bio, Inc. or SuperScript® Reverse Transcriptase of Life Technologies Corporation was used in a final concentration of 5 U/μL; an RNase inhibitor was used in a final concentration of 1 U/μL; and SpeedSTAR® HS DNA polymerase was used in a final concentration of 0.2 U/μL. FAST Buffer I and dNTP Mixture included in the product package were mixed in the concentrations specified by the manual, and used as a premixture for one-step reverse transcription real-time PCR.

The thermal cycling conditions were set as follows. When PrimeScrip® Reverse Transcriptase of Takara Bio, Inc. was used for the reverse transcription reaction, the reaction was performed at 42° C. for 10 seconds. When SuperScript® Reverse Transcriptase of Life Technologies Corporation was used, the thermal cycle conditions were 55° C. for 10 seconds. These reverse transcription reactions were performed in a serpentine microchannel located on a lower temperature heater of a PCR chip for high-speed, real-time PCR. After completion of the reverse transcription reaction, the temperature of the lower temperature heater was raised to 56° C. and the liquid was continuously delivered, whereby the process comprising heating at 96° C. for 10 seconds for hot starting and then further heating at 96° C. for 3 seconds and at 56° C. for 8 seconds was repeated for 45 cycles. The time required for 45 cycles of one-step reverse transcription real-time PCR under these conditions was 10 minutes and 20 seconds or less.

Figure 7:
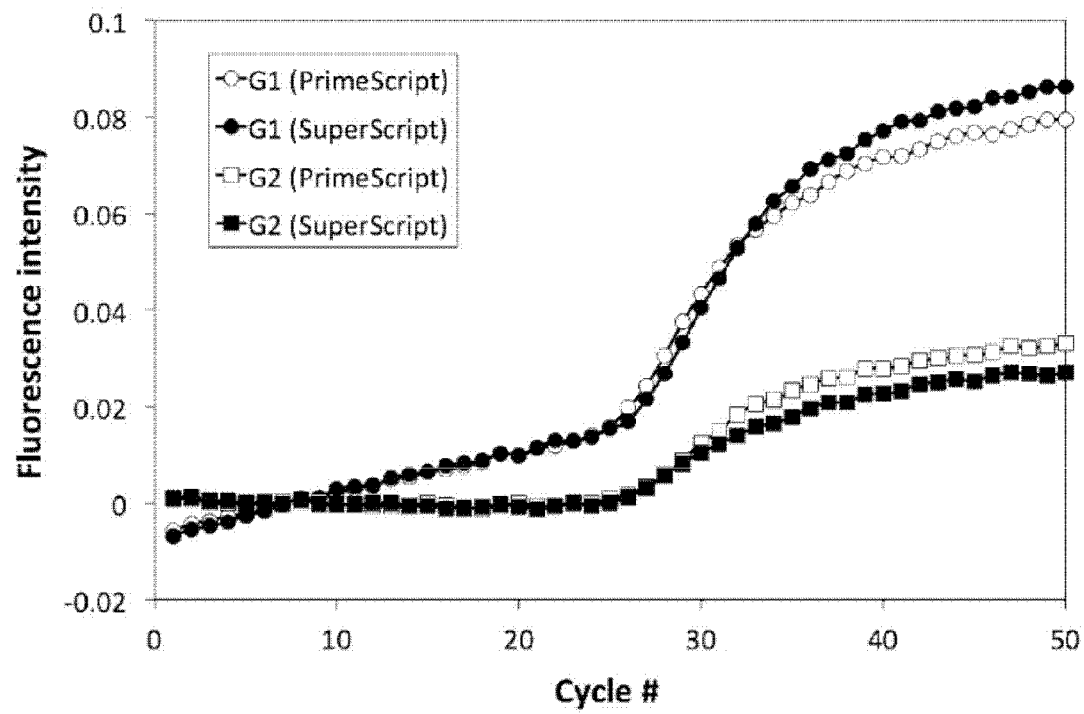
FIG. 7 shows nucleic acid amplification of RNA comprising a norovirus G1 or G2 gene sequence in high-speed, one-step reverse transcription real-time PCR using different reverse transcriptases.

The fluorescence intensity for each cycle in the high-speed, one-step reverse transcription real-time PCR was as shown in FIG. 7. When the initial concentrations of norovirus G1 and G2 genes are the same, similar sigmoid curves are obtained without depending on the type of reverse transcriptase used, and the number of cycles in which the fluorescence intensity rapidly amplified and rose was the same for both of the norovirus G1 and G2 genes.

Figure 8:
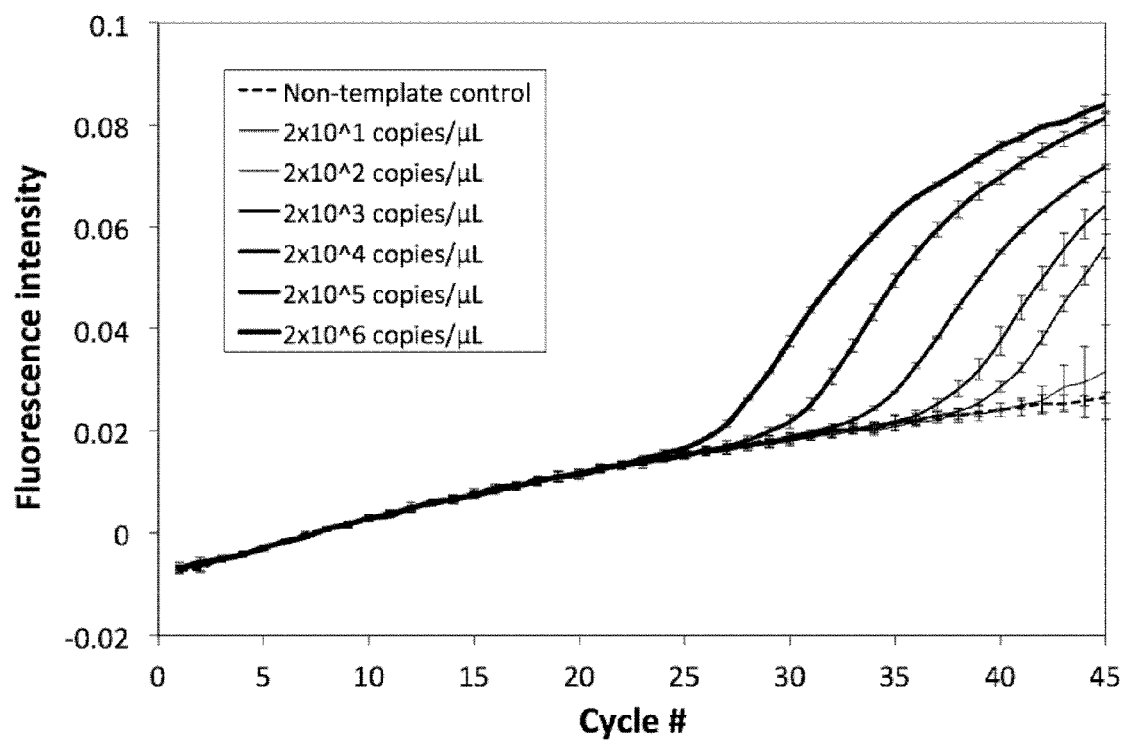
FIG. 8 shows nucleic acid amplification from different initial concentrations of RNA comprising a norovirus G1 or G2 gene sequence in high-speed, one-step reverse transcription real-time PCR.

Next, high-speed, one-step reverse transcription real-time PCR was performed by changing the initial concentrations of the RNA of norovious G1 and G2 genes. As shown in FIG. 8, the number of cycles in which fluorescence intensity rapidly amplified and rose varied depending on the initial concentration of the norovious G1 gene. The number of cycles in which rapid amplification and rise of the fluorescence intensity are observed is in the order of highest to lowest initial concentration of RNA. Accordingly, the initial concentration of RNA can be generally quantified through Ct value, which is the number of cycles in which fluorescence intensity rapidly amplifies and rises.

However, the amplification curve for the norovirus G1 gene shown in FIG. 8 confirms that the baseline is an upward-sloping curve in such a manner that the fluorescence intensity amplifies gently in accordance with thermal cycling, and then the fluorescence intensity rapidly increases from a certain number of cycles. Accordingly, it is difficult to estimate an accurate Ct value by using a usual method in which a certain level of fluorescence intensity is defined as the threshold and the number of cycles that provides a fluorescence intensity higher than the threshold is defined as the Ct value.

Accordingly, in order to detect the Ct value during the one-step reverse transcription real-time PCR even when the baseline is not a constant value, i.e., the baseline increases proportionally, the Ct value was deduced from a matrix of fluorescence intensity (two-dimensional array of the amplification curve) determined for each number of thermal cycles.

To detect the slope that rapidly rises relative to the slope below the Ct value in a two-dimensional array of the amplification curve, the following may be performed. When there is a great variation in fluorescence intensity, the running average may be obtained, if necessary. While doing so, a first forward differentiation is performed for each thermal cycle. Of the new two-dimensional array of the obtained slope, the root mean square (which may alternatively be the weighted average) of the slope of the initial stage (for example, 5 to 15 cycles, or 5 to 15 cycles immediately before each cycle) and the slope after the initial stage were compared. When a significant (for example, 5-fold or more, which may alternatively be 2-fold or more) increase in the number of cycles was observed, it was deduced as the number of cycles Ct in which the fluorescence intensity rapidly amplifies and rises.

Figure 9:
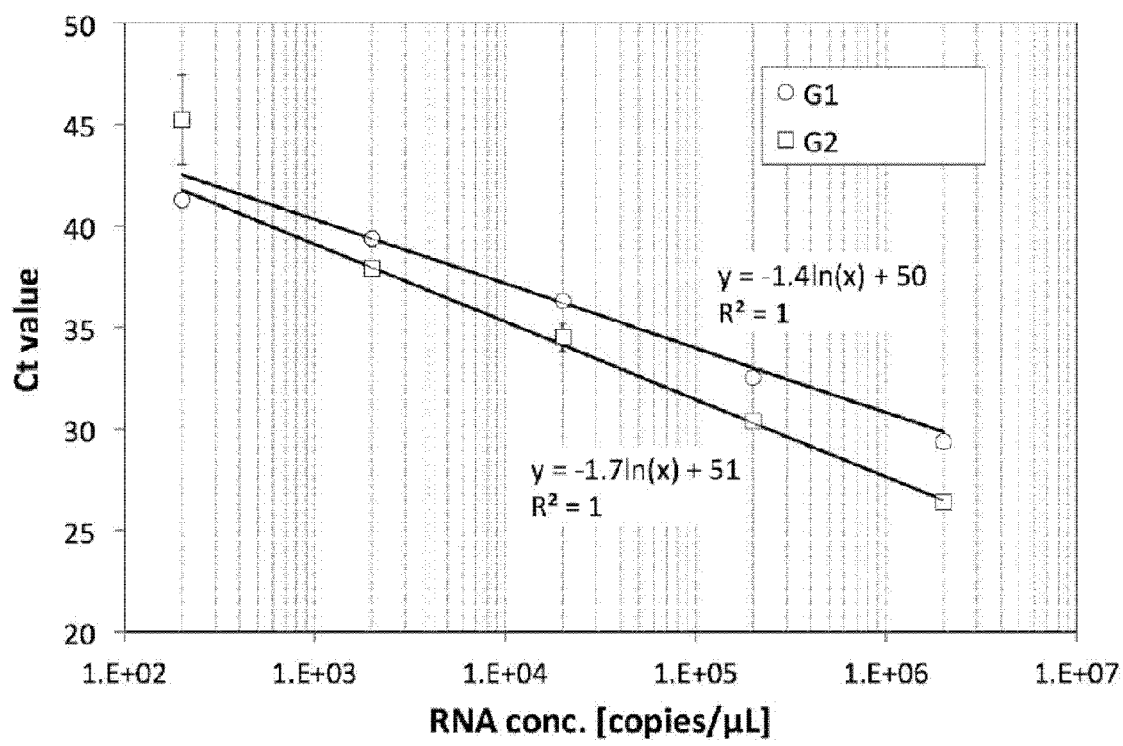
FIG. 9 shows calibration curves obtained from the number of cycles Ct in which fluorescence intensity rapidly amplifies and rises in high-speed, one-step reverse transcription real-time PCR, plotted against RNA comprising a norovirus G1 or G2 gene sequence.

FIG. 9 shows calibration curves prepared from the obtained Ct values against initial concentrations of norovirus G1 and G2 genes. Good linearity is obtained relative to each RNA concentration of the norovirus G1 and G2 genes. The Ct value can be promptly determined even during one-step reverse transcription real-time PCR, when fluorescence intensity rises rapidly. The initial RNA concentration can be calculated from the Ct value.

A feature of the present invention is a system in which the entire PCR solution passes through a microchannel in such a manner that the solution passes a fluorescence detecting point for each thermal cycle. Accordingly, even if a fluorescent dye generated by real-time PCR is non-uniformly dispersed as a fluorescent dye concentration in a PCR solution due to a lack of time to uniformly disperse the fluorescent dye in the PCR solution, which results from faster thermal cycling, all the fluorescent dyes is detected by a fluorescence detector and integrated to thereby accurately quantify the fluorescence amount for each cycle.

Accordingly, as shown in FIG. 9, in the calibration range, error bars for Ct values in the measurement of RNA concentration are very small and exact quantification with excellent reproduciblity is confirmed to be feasible.

INDUSTRIAL APPLICABILITY

The device according to the present invention is transportable and allows high-speed, real-time PCR to be performed at low cost in a clinical setting or on the spot where an infectious disease occurs. More specifically, the spread of infection can be prevented by quick confirmation of therapeutic effects and early detection of infectious diseases in livestock and poultry.

---

The invention claimed is:

1. A method for controlling a stop position of a PCR sample solution in an extension/annealing temperature zone in a microchannel of a PCR chip, wherein the microchannel comprises:
 (i) curved-channel portions corresponding to a denaturation temperature zone and an extension/annealing temperature zone,
 (ii) a linear intermediate-channel portion connecting the curved-channel portions, and
 (iii) connection portions connectable to a microblower at both ends of the microchannel,
the method comprising:
 using a microblower to deliver the PCR sample solution from the denaturation temperature zone to the extension/annealing temperature zone in the microchannel, and
 stopping the microblower upon confirming the passage of the sample solution at one place of the linear intermediate-channel portion by a fluorescence detector,
 thereby controlling the stop position of the PCR sample solution in the extension/annealing temperature zone in the microchannel of the PCR chip.

2. A method for controlling a stop position of a PCR sample solution in a denaturation temperature zone in a microchannel of a PCR chip, wherein the microchannel comprises:
 (i) curved-channel portions corresponding to a denaturation temperature zone and an extension/annealing temperature zone,
 (ii) a linear intermediate-channel portion connecting the curved-channel portions, and
 (iii) connection portions connectable to a microblower at both ends of the microchannel,
the method comprising:
 using a microblower to deliver the PCR sample solution from the extension/annealing temperature zone to the denaturation temperature zone in the microchannel, and
 stopping the microblower upon confirming the passage of the sample solution at one place of the linear intermediate-channel portion by a fluorescence detector,
 thereby controlling the stop position of the PCR sample solution in the denaturation temperature zone in the microchannel of the PCR chip.

3. A method for nucleic acid amplification using a thermal cycle in which a sample solution is reciprocated between a denaturation temperature zone and an extension/annealing temperature zone, comprising:
 using a microblower or a fan to deliver the sample solution from the denaturation temperature zone to the extension/annealing temperature zone in a microchannel, and
 using a microblower or fan to deliver the sample solution from the extension/annealing temperature zone to the denaturation temperature zone in the microchannel,
 wherein the denaturation temperature zone and the extension/annealing temperature zone are disposed on a flat surface,
 wherein the microchannel is connected to the denaturation temperature zone and the extension/annealing temperature zone, and
 wherein both ends of the microchannel are open to atmospheric pressure when a microblower or a fan is stopped.

4. A chip for nucleic acid amplification comprising at least one microchannel, wherein the at least one microchannel comprises:
 (i) only one curved-channel portion corresponding to a denaturation temperature zone,
 (ii) only one curved-channel portion corresponding to an extension/annealing temperature zone,
 (iii) only one linear intermediate-channel portion connecting the two curved-channel portions, and (iv) connection portions that can be connected to a mechanism for liquid transfer at both ends of the at least one microchannel,
 wherein the chip allows measurement of fluorescence intensity of a sample solution in the microchannel at the linear intermediate-channel portion, and
 wherein the chip comprises a substrate that comprises the microchannel formed by injection molding on a surface of the substrate.

5. The chip for nucleic acid amplification according to claim 4, wherein the chip consists essentially of plastic.

6. The chip for nucleic acid amplification according to claim 5, wherein the chip comprises a substrate that comprises the microchannel, wherein a seal is joined to the surface of the substrate on which the microchannel is formed by injection molding.

7. A chip for nucleic acid amplification comprising at least one microchannel, wherein the at least one microchannel comprises:
    (i) only one curved-channel portion corresponding to a denaturation temperature zone,
    (ii) only one curved-channel portion corresponding to an extension/annealing temperature zone,
    (iii) only one linear intermediate-channel portion connecting the two curved-channel portions, and
    (iv) connection portions that can be connected to a mechanism for liquid transfer at both ends of the at least one microchannel,
    wherein the chip allows measurement of fluorescence intensity of a sample solution in the microchannel at the linear intermediate-channel portion, and
    wherein the chip consists essentially of plastic.

* * * * *

SEQUENCE LISTING

<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<223> OTHER INFORMATION: forward primer

<400> SEQUENCE: 1
gtgtgatatc tacccgcttc gc                                    22

```
<210> SEQ ID NO 2
<211> LENGTH: 24
<212> TYPE: DNA
<213> ORGANISM: Artificial Sequence
<220> FEATURE:
<223> OTHER INFORMATION: reverse primer

<400> SEQUENCE: 2
agaacggttt gtggttaatc agga                                              24

<210> SEQ ID NO 3
<211> LENGTH: 22
<212> TYPE: DNA
<213> ORGANISM: Artificial Sequence
<220> FEATURE:
<223> OTHER INFORMATION: Artificial probe

<400> SEQUENCE: 3
tcggcatccg gtcagtggca gt                                                22

<210> SEQ ID NO 4
<211> LENGTH: 16
<212> TYPE: DNA
<213> ORGANISM: Artificial Sequence
<220> FEATURE:
<223> OTHER INFORMATION: forward primer

<400> SEQUENCE: 4
gtttgatcct ggctca                                                       16

<210> SEQ ID NO 5
<211> LENGTH: 18
<212> TYPE: DNA
<213> ORGANISM: Artificial Sequence
<220> FEATURE:
<223> OTHER INFORMATION: Artificial probe

<400> SEQUENCE: 5
cgggtgagta atgtctgg                                                     18

<210> SEQ ID NO 6
<211> LENGTH: 16
<212> TYPE: DNA
<213> ORGANISM: Artificial Sequence
<220> FEATURE:
<223> OTHER INFORMATION: reverse primer

<400> SEQUENCE: 6
ctttggtctt gcgacg                                                       16

<210> SEQ ID NO 7
<211> LENGTH: 15
<212> TYPE: DNA
<213> ORGANISM: Artificial Sequence
<220> FEATURE:
<223> OTHER INFORMATION: reverse primer

<400> SEQUENCE: 7
gcatggctgc atcag                                                        15

<210> SEQ ID NO 8
<211> LENGTH: 17
<212> TYPE: DNA
<213> ORGANISM: Artificial Sequence
<220> FEATURE:
<223> OTHER INFORMATION: reverse primer
```

-continued

<400> SEQUENCE: 8
ctgacttaac aaaccgc                                                     17

<210> SEQ ID NO 9
<211> LENGTH: 18
<212> TYPE: DNA
<213> ORGANISM: Artificial Sequence
<220> FEATURE:
<223> OTHER INFORMATION: reverse primer

<400> SEQUENCE: 9
taccagggta tctaatcc                                                    18

<210> SEQ ID NO 10
<211> LENGTH: 20
<212> TYPE: DNA
<213> ORGANISM: Artificial Sequence
<220> FEATURE:
<223> OTHER INFORMATION: forward primer
<220> FEATURE:
<221> NAME/KEY: misc_feature
<222> LOCATION: (12)..(12)
<223> OTHER INFORMATION: n is a, c, g, or t

<400> SEQUENCE: 10
cgytggatgc gnttycatga                                                  20

<210> SEQ ID NO 11
<211> LENGTH: 20
<212> TYPE: DNA
<213> ORGANISM: Artificial Sequence
<220> FEATURE:
<223> OTHER INFORMATION: Artificial probe

<400> SEQUENCE: 11
agatygcgat cycctgtcca                                                  20

<210> SEQ ID NO 12
<211> LENGTH: 20
<212> TYPE: DNA
<213> ORGANISM: Artificial Sequence
<220> FEATURE:
<223> OTHER INFORMATION: Artificial probe

<400> SEQUENCE: 12
agatcgcggt ctcctgtcca                                                  20

<210> SEQ ID NO 13
<211> LENGTH: 21
<212> TYPE: DNA
<213> ORGANISM: Artificial Sequence
<220> FEATURE:
<223> OTHER INFORMATION: reverse primer

<400> SEQUENCE: 13
cttagacgcc atcatcatty a                                                21

<210> SEQ ID NO 14
<211> LENGTH: 26
<212> TYPE: DNA
<213> ORGANISM: Artificial Sequence
<220> FEATURE:
<223> OTHER INFORMATION: forward primer
<220> FEATURE:
<221> NAME/KEY: misc_feature
<222> LOCATION: (9)..(9)
<223> OTHER INFORMATION: n is a, c, g, or t

```
<400> SEQUENCE: 14
cargarbcna tgttyagrtg gatgag                                      26

<210> SEQ ID NO 15
<211> LENGTH: 20
<212> TYPE: DNA
<213> ORGANISM: Artificial Sequence
<220> FEATURE:
<223> OTHER INFORMATION: Artificial probe

<400> SEQUENCE: 15
tgggagggsg atcgcratct                                             20

<210> SEQ ID NO 16
<211> LENGTH: 21
<212> TYPE: DNA
<213> ORGANISM: Artificial Sequence
<220> FEATURE:
<223> OTHER INFORMATION: reverse primer

<400> SEQUENCE: 16
tcgacgccat cttcattcac a                                           21
```